United States Patent [19]
Hernandez et al.

[11] Patent Number: 5,607,406
[45] Date of Patent: *Mar. 4, 1997

[54] RAPID EXCHANGE SEGMENTED CATHETER

[75] Inventors: Ernesto Hernandez, Miami; Francisco O. Castillo, Miami Lakes; Israel Pagan, Miami, all of Fla.

[73] Assignee: Cordis Corporation, Miami Lakes, Fla.

[*] Notice: The portion of the term of this patent subsequent to May 17, 2014, has been disclaimed.

[21] Appl. No.: 589,502

[22] Filed: Jan. 22, 1995

Related U.S. Application Data

[62] Division of Ser. No. 243,283, May 17, 1994, Pat. No. 5,507,731.

[51] Int. Cl.$^6$ .................................................. A61M 5/00
[52] U.S. Cl. ........................... 604/264; 604/283; 604/905
[58] Field of Search ..................................... 604/264, 283, 604/43, 49, 52, 53, 95, 96, 905; 128/657, 772

[56] References Cited

U.S. PATENT DOCUMENTS

| | | |
|---|---|---|
| 4,748,982 | 6/1988 | Horzewski et al. . |
| 4,762,129 | 8/1988 | Bonzel . |
| 5,040,458 | 8/1991 | Yock . |
| 5,205,822 | 4/1993 | Johnson et al. . |
| 5,234,407 | 8/1993 | Tierstein et al. . |
| 5,269,759 | 12/1993 | Hernandez et al. . |
| 5,312,352 | 5/1994 | Leschinsky et al. . |
| 5,360,395 | 11/1994 | Utterberg . |
| 5,507,731 | 4/1996 | Hernandez et al. ............... 604/264 |

Primary Examiner—John D. Yasko
Attorney, Agent, or Firm—Gerstman, Ellis & McMillin, Ltd.

[57] ABSTRACT

An intravascular catheter is described which is capable of rapid exchange without dislodging of a guidewire and without the presence of side apertures in the catheter. The catheter comprises a plurality of segments which are secured together in end-to-end relation, but which are separable into separated segments by the user while the distal catheter end is inserted in the vascular system of a patient.

14 Claims, 1 Drawing Sheet

U.S. Patent    Mar. 4, 1997    5,607,406
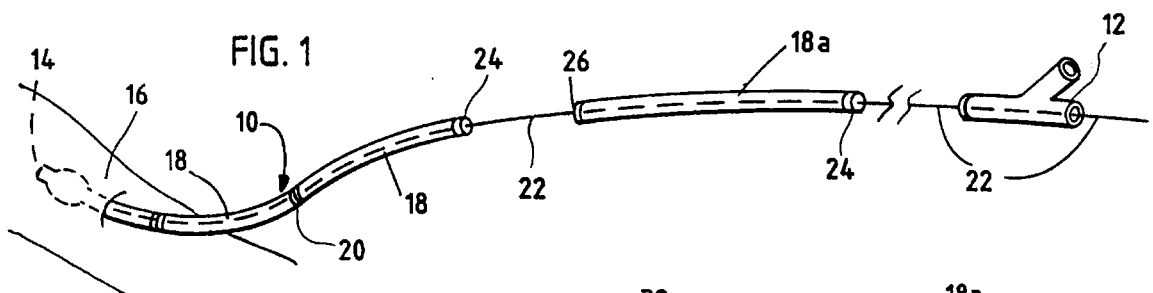
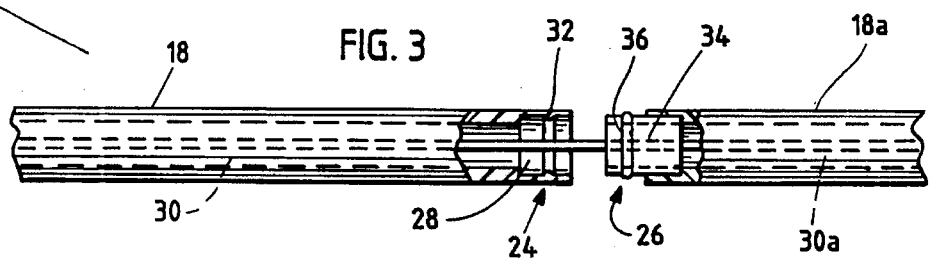

RAPID EXCHANGE SEGMENTED CATHETER

CROSS REFERENCE TO RELATED APPLICATION

This application is a division of application Ser. No. 08/243,283, filed May 17, 1994, now U.S. Pat. No. 5,507,731.

BACKGROUND OF THE INVENTION

"Rapid exchange"-type balloon dilatation catheters are catheters which are capable of advancement into the vascular system of a patient along a preemplaced guiding catheter or guidewire, for balloon angioplasty or the like. Typically in a rapid exchange catheter, the guidewire occupies a lumen of the catheter in only a distal portion thereof. With respect to the catheter proximal portion, the guidewire typically exits from the internal catheter lumen through a hole or slit, and extends along the side of the catheter, being typically retained in that position by a guiding catheter in which both the catheter and the guidewire are contained. Examples of rapid exchange catheters include those disclosed in Horzewski, et al. U.S. Pat. No. 4,748,982, Bonzel U.S. Pat. No. 4,762,129, Yock U.S. Pat. No. 5,040,548, and Johnson U.S. Pat. No. 5,205,822.

A chief advantage of rapid exchange catheters lies in the fact that hey can be removed from an advanced position in the vascular system of a patient, being withdrawn along the guidewire without inadvertently causing the guidewire to withdraw as well. Thus there is no need for a guidewire extension, which is attached to the proximal end of the guidewire to give the guidewire more length.

As another technique and device for rapid exchange catheters, Teirstein, et al. U.S. Pat. No. 5,234,407 discloses the use of an "exchange catheter" which is inserted between the guidewire and the balloon dilatation catheter before the balloon dilatation catheter is withdrawn. The guidewire extends alongside such a catheter, passing through a pair of apertures in the exchange catheter. This can serve in proper circumstances to prevent the inadvertent withdrawal of the guidewire as the balloon dilatation catheter is withdrawn.

However, there are disadvantages involved in having the guidewire occupy a position alongside rather than inside of a proximal portion of the catheter.

In accordance with this invention, another approach is provided for imparting a rapid exchange capability to a balloon dilatation catheter carried on a guidewire, without the need for a guidewire extension unit and without the need for a portion of the guidewire to pass through the catheter wall and reside outside of a proximal portion of the catheter. Thus the steering of the catheter of this invention can be improved. Also, the guidewire lumen of such a catheter can be pressurized for desired fluid flow without the risk of side leakage through any aperture, slit, or frangible area in the catheter wall.

DESCRIPTION OF THE INVENTION

By this invention an intravascular catheter is provided which comprises proximal and distal ends, said catheter also having a balloon connected to an inflation lumen. The balloon is carried adjacent the distal end of the catheter, as is conventional.

In accordance with this invention, the catheter comprises a plurality of segments which are secured together in end-to-end relation, but which are separable into separated segments by the user while the distal catheter end is inserted into the vascular system of a patient.

Thus, the catheter of this invention is capable of insertion into the vascular system of a patient along a guidewire, or withdrawal therefrom along the guidewire, by either sequentially assembling or disassembling the respective segments of the catheter as the catheter is advanced or withdrawn. Thus a portion of the guidewire can always be grasped by the physician, because of the use of the separable segments. For example, upon withdrawal of the catheter, in the conventional situation, the catheter withdraws to completely enclose that portion of the guidewire which is outside of the body. Accordingly, further withdrawal of the catheter may result in a retraction of the guidewire, which is potentially catastrophic. Once the guidewire has penetrated through a stenosis, it may never again be possible for the guidewire to penetrate that stenosis if it is ever withdrawn prior to the angioplasty procedure. Thus, a potentially life saving advantage may be lost if the guidewire is inadvertently withdrawn while the physician is removing a balloon catheter. A physician may need to remove such a catheter if it turns out to be less suitable than a different catheter, which will be inserted along the guidewire as soon as the old catheter has been removed.

Thus, by this invention, as the catheter is withdrawn from the arterial vascular system of the patient, one may separate its longitudinal segments, one by one, as they appear outside of the body, before the catheter gets long enough in its portion external to the body to completely engulf the guidewire portion outside of the body. Thus, the physician can always grasp the guidewire as the catheter is being withdrawn, to prevent its accidental withdrawal along with the catheter.

Similarly, a catheter to be applied to the body may start in disassembled form. The first segment of the catheter which defines the distal end and which carries the balloon may be advanced into the arteriovenous system of the patient along the guidewire. Then, when that first segment is almost completely advanced, one may place a second segment on the guidewire, with the segment being short enough to always permit the physician to grasp the guidewire, at a point between the first segment and a next segment, and then later at the proximal end of the guidewire as the segment is advanced. The first and second segments are then locked together in a conventional manner, or by use of any of the connector structures disclosed below. The catheter is then advanced along the guidewire, with the segments being added one by one in such a manner as described above that the guidewire can always be gripped by the physician, with the segments locking together as described.

In one embodiment of the catheter of this invention, the inflation lumen comprises a separate tube that is unconnected to the segments, other than the first segment that carries the balloon. This facilitates the use of a screw-threaded connection to connect the segments together, in which one end of each catheter segment defines an axially extending, screw threaded member which enters into a screw threaded recess of the segment with which it connects. Except typically for the first and last segments, the respective segments of the catheter of this invention can be of identical design.

Alternatively, the segments can connect together with other known connections, for example, a snap-fit connection, a magnetic connection, or a twist locking slot-type connection, also known as a bayonet type connection.

Thus, the catheter of this invention can be assembled and disassembled into end-connected sections as the catheter is advanced, or withdrawn, to provide a rapid exchange capability for the catheter, without the use of side apertures or a guidewire extension.

DESCRIPTION OF THE DRAWINGS

FIG. 1 is a partial, perspective view of a catheter for angioplasty, shown with its distal end inserted in an artery of a patient while surrounding a guidewire, and further showing how the catheter can be separated into separate sections;

FIG. 2 is an enlarged, elevational view of another embodiment of the catheter of this invention, shown similarly with its distal end in the artery of a patient, and showing separable catheter sections being separated at an intermediate position;

FIG. 3 is an enlarged, fragmentary, elevational view of two separated catheter sections of the embodiment of FIG. 2 showing the connection system between the catheter segments;

FIG. 4 is an elevational view of another embodiment for a connection system between catheter sections;

FIG. 5 is an elevational view with a portion broken away of yet another embodiment of a connector system for catheter sections;

FIG. 6 is a sectional view of another embodiment for a connection system between catheter sections; and FIG. 7 is a sectional detail of the embodiment of FIG. 6.

DESCRIPTION OF SPECIFIC EMBODIMENTS

Referring to FIG. 1, an intravascular catheter 10 is disclosed having a proximal end 12, and a distal end 14 shown to be penetrating the skin 16 of a patient to enter the arterial system. The catheter may carry a balloon adjacent distal end 14 and an inflation lumen in a generally conventional manner, except as otherwise disclosed herein.

In accordance with this invention, catheter 10 comprises a plurality of segments 18, which may be secured together in end-to-end relation, but also may be separable into separated segments, as illustrated by segment 18a, while the distal catheter end 14 is inserted in the vascular system of a patient, as shown in FIG. 1. Thus, catheter 10 may be disassembled into a plurality of separate segments, and then reassembled so that the respective segments 18 are secured together by segments 20.

Thus, the catheter may be threaded onto a guidewire 22, with end 14 being inserted into the arterial system of the patient. As the catheter is advanced, the respective segments 18, 18a are sequentially threaded along the guidewire and attached together at respective connections 20, so that the portion of catheter 10 which extends outwardly from the skin of the patient is never longer than the corresponding portion of guidewire 22 which extends outwardly from the patient's skin. This permits the surgeon to continuously grasp guidewire 22 to control its position in the patient at all times while the catheter is being advanced, the catheter being assembled as it is advanced.

Similarly, on withdrawal of the catheter, the respective catheter sections, beginning at the proximal end 12 of the catheter, may be sequentially disassembled and taken off guidewire 22, so that the retracting catheter portion which is outside of the skin of the patient may never be longer than the corresponding portion of guidewire 22 which is outside of the patient, thus permitting the physician to grasp the guidewire at all times, primarily to prevent accidental guidewire retraction as the catheter is being retracted.

Referring to FIG. 3, a detail of the respective connectors 24, 26 of a pair of catheter sections 18, 18a is shown. Numerous different designs of connectors 24, 26 may be used in accordance with this invention, FIG. 3 shows a particular design in which connector 24 on catheter section 18 comprises a female receptacle 28 which communicates with the lumen 30 of catheter section 18. The inner wall of receptacle 28 defines a series of bumps or projections 32.

Male connector portion 26, carried on one end of catheter section 18a, comprises a sleeve 34 which is carried by the catheter and has a lumen which communicates with lumen 30a of catheter 18a. Sleeve 34 also defines an annular, outwardly extending rib 36. The respective connector sections 18, 18a thus engage each other in a telescoping manner, with connector 26 entering into connector 24 until annular rib 36 snaps past projections 32, to provide a locked and sealed relationship, rather in the manner of covers for PILOT pens.

The catheter sections 18, 18a may be separated again with a vigorous pull, but the connection is strong enough to permit the catheter to be withdrawn by a gentler pull without accidentally breaking such connections.

Each of the catheter sections 18 except for those catheter sections which respectively define the catheter ends 12, 14 may define a connection 24 on one end and another connector 26 on the other end, so that the central, intermediate catheter sections 18 may be interchangeably used in building a catheter of any desired length, while being of identical design to each other.

Referring to FIG. 4, two catheter sections 18b are disclosed, being securable together in end-to-end relation in the manner of the previous embodiment, but with a different type of connection.

In this embodiment, the respective connectors 40, 42 at the ends of the catheter sections 18b each comprise a pair of tubular magnets. Connector magnet 40 is secured to its catheter section with the positive pole facing outwardly, while connector magnet 42 is a tubular magnet with its negative pole facing outwardly. Thus, the respective ends of the connectors 40, 42 are attracted to each other by magnetic force. One of the tubular ends, specifically end 42, may define an inner, tubular, stepped portion 44 which fits into an annular, stepped recess 46 in the other magnetic connector 40.

Steps 44 and 46 may be of identical, interlocking geometric shapes to permit the respective catheter section ends to mate together in snap-fit or other tight relationship only in a single position. By this means, inflation lumens which are defined in the catheter sections in off-center manner may be aligned. For example, the geometric shape defined by sections 44, 46 may be a polygon such as a rectangle or a pentagon in which one or more of the sides are curved, to assure mating in only one angular relation, to thus assure alignment of the laterally positioned inflation lumen, when such a lumen is present.

Thus, when brought together, the respective catheter sections 18b securely and firmly bond together by magnetic force until they are forcefully separated, as may happen outside of the body to disassemble the catheter as the catheter is being withdrawn in accordance with the previous description.

Referring to FIG. 5, another type of connection 48, 50 for catheter sections 18c is shown. Connector 48 may comprise a tubular extension of its catheter section 18c. Typically, the tubular extension 48 may be made of metal, and bonded to an end of the catheter 18c along an annular bond line 51. Metal connector sleeve 48 comprises an angled track 52, and an inner wall 54 separated from an outer wall 56 by an annular slot 58 which contains a spring 60.

Connector 50, carried on an adjacent catheter section 18c, is a tubular member which may also be made of metal, and which comprises an external projection 62, which is proportioned to fit into track 52. Thus, the respective connector sections may be axially pressed together so that tubular connector 50 enters cylindrical slot 58 and compresses spring 60, while projection 62 slides in track 52. One then rotates the catheter sections to cause projection 62 to occupy the circumferential portion 64 of slot 52, to lock the two catheter sections together.

In all of the above embodiments, each catheter section except for the proximal and distal sections may carry one kind of the mating connectors on one end and the other kind of mating connectors on the other end, so that the catheter sections may be connected to each other to assemble a desired catheter of various lengths.

Referring to FIGS. 6 and 7, another connector embodiment 66, 68 for the catheters described above is disclosed. The respective catheter sections 18d each define a main lumen 70, and an inflation lumen 72, which may connect with a balloon carried by a distal catheter section.

Connector 66 defines a series of screw threads 74 which receive the mating screw threads 76 of connector 68. FIG. 6 shows how the respective inflation lumens 72 can connect as the screw threaded portion 74, 76 are brought together.

Projection 78, carried by connector 66, restricts the relative advance of the screw threaded members together, so that an annular chamber 80 is defined which connects with each of the inflation lumens 72, irrespective of the relative rotational positions of the lumens 72. In other words, there will be a flow connection between the respective lumens 72 of connectors 66, 68 at any angular position that the lumens 72 may take with respect to each other as they are rotated by the screw threads, with the connection being through the annular chamber 80 that is formed when the two connectors are brought together in screw-threaded, tight relationship. Also, it can be seen that the structure seals inflation lumen 72 from the guidewire lumen 70, permitting inflation and deflation of the balloon irrespective of the relative angular positions of the inflation lumens 72.

Referring to FIG. 2, another embodiment of the segmented catheter of this invention 10a is disclosed. The distal end 14a of the catheter is shown to be placed through the skin of the patient 84 and into an artery. The catheter comprises a plurality of segments 18e, which are secured together in end-to-end relation as in the previous embodiments, but which are separable into separated segments by the user while the distal catheter end 14a is inserted into the vascular system of a patient.

The particular connectors 86, 88 may be of any desired design, for example any of the designs disclosed in the previous embodiments. While only two segments 18e of the catheter are shown, it is understood that an unlimited number of segments may be connected together to define the catheter, typically terminating in a proximal end segment similar to segment 12 above.

In accordance with this invention, the distally positioned balloon 90 of catheter 10a carries a separate, continuous inflation tube 92, which communicates with balloon 90, but comprises a separate tube that is unconnected to the respective segments 18e, other than the segment which carries balloon 90.

As shown, separate inflation tube 92 may lie alongside the remainder of the catheter, entering the patient through the same incision 93 to enter the arterial system, typically passing through a conventional catheter sheath introducer and a guiding catheter in accordance with the usual practice. These added catheters are deleted from the drawing for purposes of clear illustration. The proximal end 94 of inflation tube 92 may communicate with a source of pressurized fluid such as a syringe, adjacent the proximal end of the catheter, for inflating and deflating balloon 90 as is desired.

This structure eliminates the technical problem of providing a connection system between the respective separable catheter segments that assures that inflation lumen sections defined within the catheter sections line up with each other.

Thus, a catheter is provided which may be threaded on a guidewire through the vascular system of a patient for angioplasty, angiography, or the like, in which the catheter may be exchanged without the need for a guidewire extension or for side apertures or slits in the catheter itself.

Also, catheters may be "tailor made" to an extent, by the appropriate selection of catheter segments to vary the length of the catheter, or varying as desired the expansion diameter of the balloon and/or other characteristics of the distal tip of the catheter, as well as the other portions thereof. Thus, by the simple selection of particular catheter segments from a variety of catheter segments, one can provide, even at the site of the surgery, a catheter having a desired distal tip and balloon, while the length of the catheter may also be adjusted by selection of the number of segments. Other characteristics of the catheter such as its flexibility and diameter at various areas along its length may also be specifically selected.

Furthermore, the catheter may be withdrawn, and the distal catheter segment may be replaced by another catheter segment having a balloon of different size, for example, or a distal tip of smaller diameter. Then, essentially the same catheter except for the distal tip segment may be reinserted into the patient, for a significant saving of time and expense.

The above has been offered for illustrative purposes only, and is not intended to limit the scope of the invention of this application, which is as defined in the claims below That which is claimed is:

1. A method for exchanging a catheter in the vascular system of a patient, which comprises the steps of:

introducing a guidewire into said vascular system;

introducing a catheter into said vascular system over said guidewire, said catheter having at least a distal section and a connected proximal section;

withdrawing said catheter from said vascular system by first removing only said proximal section while restraining said guidewire;

thereafter removing said distal section while restraining said guidewire.

2. A method as defined by claim 1, in which the step of introducing includes first introducing only said distal section over the guidewire and thereafter introducing said proximal section over the guidewire and connecting said proximal section to said distal section.

3. A method as defined in claim 1, in which said proximal section comprises a plurality of connected sections and the step of removing said proximal section comprises the step of removing said plurality of sections, one by one while restraining said guidewire.

4. A method as defined by claim 1, in which said segments connect together with a screw threaded connection and said proximal section removing step comprises unscrewing said proximal section from said distal section.

5. A method as defined in claim 1, in which said segments connect together with a snap-fit connection and said proximal section removing step comprises unsnapping said proximal section from said distal section.

6. A method as defined by claim 1, in which said segments connect together with a twist locking slot-type connection and said proximal section removing step comprises twisting and unlocking said proximal section from said distal section.

7. A method as defined by claim 1, in which said segments connect together with a magnetic connection and said proximal section removing step comprises demagnetic-coupling said proximal section from said distal section.

8. A catheter for introduction into and withdrawal from the vascular system of a patient over a guidewire in said vascular system, which comprises:

said catheter having a distal section and a proximal section;

said distal section and said proximal section being alternatively connectable and separable;

said catheter being adapted for introduction into said vascular system over said guidewire and for withdrawal from said vascular system by removing said proximal section while restraining said guidewire and thereafter removing said distal section while restraining said guidewire.

9. A catheter as defined by claim 8, said proximal section comprising a plurality of sections that are connectable and separable.

10. A catheter as defined by claim 8, said sections being connectable together with a screw-threaded connection.

11. A catheter as defined by claim 8, in which said sections are connected together with a snap-fit connection.

12. A catheter as defined by claim 8, in which said sections are connected together with a twist-locking slot-type connection.

13. A catheter as defined by claim 8, in which said sections connect together with a magnetic connection.

14. A catheter as defined by claim 8, said distal section carrying an inflatable balloon and defining a lumen for inflating said balloon.

* * * * *